(12) United States Patent
May et al.

(10) Patent No.: US 6,664,286 B1
(45) Date of Patent: Dec. 16, 2003

(54) SEROTONERGIC 5HT$_2$ AGONISTS FOR TREATING GLAUCOMA

(75) Inventors: Jesse A. May, Fort Worth, TX (US); Thomas R. Dean, Weatherford, TX (US); Najam A. Sharif, Arlington, TX (US); Mark R. Hellberg, Arlington, TX (US)

(73) Assignee: Alcon Manufacturing, Ltd., Fort Worth, TX (US)

( * ) Notice: Subject to any disclaimer, the term of this patent is extended or adjusted under 35 U.S.C. 154(b) by 0 days.

(21) Appl. No.: 09/787,332

(22) PCT Filed: Sep. 3, 1999

(86) PCT No.: PCT/US99/19888

§ 371 (c)(1),
(2), (4) Date: Mar. 15, 2001

(87) PCT Pub. No.: WO00/16761

PCT Pub. Date: Mar. 30, 2000

Related U.S. Application Data

(60) Provisional application No. 60/101,067, filed on Sep. 18, 1998.

(51) Int. Cl.$^7$ ............................................. A61K 31/405
(52) U.S. Cl. ........................ 514/415; 514/392; 514/913
(58) Field of Search ................................ 514/415, 392, 514/913

(56) References Cited

U.S. PATENT DOCUMENTS

| | | | |
|---|---|---|---|
| 4,487,773 A | 12/1984 | Temple, Jr. et al. | 424/250 |
| 4,659,706 A | 4/1987 | Bondinell et al. | 514/213 |
| 5,011,846 A | 4/1991 | Gittos et al. | 514/294 |
| 5,106,555 A | 4/1992 | Kobayashi et al. | 264/112 |
| 5,290,781 A | 3/1994 | Espino et al. | 514/259 |
| 5,494,928 A | 2/1996 | Bos | 514/415 |
| 5,538,974 A | 7/1996 | Ogawa et al. | 514/253 |
| 5,545,644 A | 8/1996 | Macor et al. | 514/323 |
| 5,571,833 A | 11/1996 | Kruse et al. | 514/414 |
| 5,578,612 A | 11/1996 | Macor et al. | 514/323 |
| 5,646,173 A | 7/1997 | Bos et al. | 514/411 |
| 5,652,272 A | 7/1997 | Ogawa et al. | 514/652 |
| 5,693,654 A | 12/1997 | Birch | 514/323 |
| 5,861,425 A | 1/1999 | Audia et al. | 514/411 |

FOREIGN PATENT DOCUMENTS

| | | |
|---|---|---|
| EP | 0 522 226 A1 | 1/1993 |
| EP | 0 771 563 A2 | 5/1997 |
| EP | 0 863 136 A1 | 9/1998 |
| WO | 92/20338 | 11/1992 |
| WO | 94/03162 | 2/1994 |
| WO | 96/29074 | 9/1996 |
| WO | 97/17345 | 5/1997 |
| WO | 97/33579 | 9/1997 |
| WO | 98/18458 | 5/1998 |
| WO | 98/30546 | 7/1998 |
| WO | 98/30548 | 7/1998 |
| WO | 98/31354 | 7/1998 |
| WO | 98/56768 | 12/1998 |
| WO | 99/11619 | 3/1999 |

OTHER PUBLICATIONS

Zifa, et al. "5–Hydroxytryptamine Receptors," *Pharmacological Reviews*, vol. 40(3):401–458, 1992.

Hoyer, et al., "VII. International union of pharmacology classification of receptors for hydroxytryptamine (serotonin)," *Pharmacological Review*, vol. 46(2):157–203, 1994.

Tobin, et al., "Evidence for the presence of serotonergic nerves and receptors in the iris–ciliary body complex of the rabbit," *Journal of Neuroscience*, vol. 8(10):3713–3721, 1988.

Martin, et al., "The structure and signalling properties of 5–HT receptors: an endless diversity?"*Trends in Pharmacology*, vol. 19:2–7, Jan. 1998.

Martin, et al., "Serotonin in human aqueous humor," *Ophthalmology*, vol. 95(9): 1221–1226, Sep. 1988.

Mallorga, et al., "Characterization of serotonin receptors in the iris + ciliary body of the albino rabbit," *Eye Research*, vol. 6(3):527–532, 1987.

Chidlow, et al., "Characteristics of [3H]5–Hydroxytryptamine binding to iris–ciliary body tissue of the rabbit," *Investigative Ophthalmology & Visual Science*, vol. 36(11):2238–2245, Oct. 1995.

Tobin, et al., "Evidence for the presence of serotonin receptors negatively couplde to adenylate cyclase in the rabbit Iris–ciliary body," *Journal Neurochemistry*, vol. 53(3):686–690, 1989.

Barnett, et al., "The presence of serotonin (5–HT1) receptors negatively coupled to adenylate cyclase in rabbit and Human iris–ciliary processes," *Exp. Eye Research*, vol. 57:209–216, 1993.

Osborne, "Serotonin and melatonin in the iris/ciliary processes and their involvement in intraocular pressure," *ACTA Neurobiol. Exp*, vol. 54(Suppl.):57–64, 1994.

Gupta, et al., "Therapeutic potentials of 5–HT receptor modulators", *Indian Journal of Pharmacology*, vol. 26:94–107, 1994.

Chu, et al., "8OH–DPAT–Induced ocular hypotension: sites and mechanisms of action," *Exp. Eye Research*, vol. 69(2):227–238, Aug. 1999.

Huang, et al., "5–HT2 receptor–mediated potentiation of dopamine synthesis and central serotonergic deficits", *European Journal of Pharmacology*, vol. 238(2–3):291–296, Jul. 20, 1993.

(List continued on next page.)

*Primary Examiner*—Zohreh Fay
(74) *Attorney, Agent, or Firm*—Teresa J. Schultz

(57) ABSTRACT

Compounds with 5HT$_2$ receptor agonist activity useful for treating glaucoma, including lowering intraocular pressure. Compositions and methods for their use are also disclosed.

11 Claims, No Drawings

OTHER PUBLICATIONS

Glennon, et al., "A comparison of the behavioral properties of (±)-,(−)-, and (+)-5-Methoxy-(χ-Methyltryptamine," *Biological Psychiatry*, vol. 18(4):493–498, 1983.

Mongeau, et al., "Activation of 5–HT3 receptors enhances the electrically evoked release of [3H]noradrenaline in rat Brain limbic structures," *European Journal of Pharmacology*, vol. 256:269–279, 1994.

Mano, et al., "The effect of Anplag®(Sarpogrelate HCL), new selective 5–HT2 antagonist on intraocular pressure in rabbits," *Investigative Ophthalmology & Visual Science*, vol. 36(4):S719, 1995.

Takenaka, et al., "The effect of Anplag®(Sarpogrelate HCL), novel selective 5–HT2 antagonist on intraocular pressure in Glaucoma patients," *Investigative Ophthalmology & Visual Science*, vol. 36(4):S734, Mar. 15, 1995.

Baxter, et al., "5–HT2 receptor subtypes: a family re-united?" *Trends in Pharmacol.* vol. 16:105–110, 1995.

Nichols, et al., "Synthesis and serotonin receptor affinities of a series of enantiomers of α-methyltryptamines: evidence for the binding conformation of tryptamines at serotonin 5–HT1B Receptors," *J. Med. Chem.*, vol. 31:1406–1412, 1988.

Parker et al., "A novel (benzodifuranyl)aminoalkane with extremely potent activity at the 5–HT$_{2A}$ receptor[1]," *Journal Med. Chem.*, vol. 41:5148–5149, 1998.

Vangveravong, et al., "Synthesis and serotonin receptor affinities of a series of trans–2–(Indole–3–yl)cyclopropylamine derivatives," *Journal Med. Chem.*, vol. 41:4995–5001, 1998.

Albertini, et al., Suppression of mutagenic activity of a series of 5HT$_{2c}$ receptor agonists by the incorporation of a gem–dimethyl group:SAR using the Ames test and a DNA unwinding assay; *Mutagenesis*, vol. 13(4):397–403, 1998.

Monte, et al., "Dihydrobenzofuran analogues of hallucinogens. 4[1] Mescaline derivatives[2]," *Journal Med. Chem.*, vol. 40:2997–3008, 1997.

Bös, et al., "Synthesis, pharmacology and therapeutic potential of 10–methoxypyrazino[1,2-a]indoles, partial agonists At the 5HT2c receptor," *Eur. Journal Med. Chem.*, vol. 32:253–261, 1997.

Bös, et al., "Novel agonists of 5HT2c receptors. Synthesis and biological evaluation of substituted . . . ,"*J. Med. Chem.*, vol. 40:2762–2769, 1997.

Munte, et al., "Dihydrobenzofuran analogues of hallucinogens. 3.[1] Models of 4–substituted (2,5–dimethoxyphenyl) . . . ," vol. 39:2953–2961, 1996.

Glennon, et al., Influence of amine substitutes on 5–HT$_{2A}$ vs. 5–HT$_{2C}$ binding of phenylalkyl–and indolylalkylamines *Journal Med. Chem.*, vol. 37:1929–1935, 1994.

Macor, et al., "The synthesis of conformationally/rotationally restricted analogs of the neurotransmitter serotonin," *Tetrahedron Letters*, vol. 35(1):45–48, 1994.

Macor, et al., "Synthesis and serotonergic pharmacology of the enantiomers of 3–[(N–methylpyrrolidin–2–yl)methyl] –5–. . . ," *J. Med. Chem.*, vol. 35:4503–4505, 1992.

Macor, et al., "1–(2–Aminoethyl)–3–methyl–8,9–dihydropyrano[3,2–3]indole: A rotationally restricted phenolic analog . . . ," *Journal Med. Chem.*, vol. 35:3625–3632, 1992.

Glennon, et al., "Binding of phenylalkylamine derivatives at 5–HT1C and 5–HT2 serotonin receptors: Evidence for a lack of selectivity," *J. Med. Chem.*, vol. 35:734–740, 1992.

Seggel, et al., "A structure–affinity study of the binding of 4–substituted analogues of 1–(2,5–Dimethoxyphenyl) . . . ," *J. Med. Chem.*, vol. 33:1032–1036, 1990.

Bowen, et al., "Nonlinear regression using spreadsheets," *Trends in Pharmacol. Sci.*, vol. 16:413–417, 1995.

Griffin, et al., "Pharmacological characterization of an FP prostaglandin receptor on rat vascular smooth muscle . . . ," *The Journal of Pharmacology and Experimental Therapeutics*, vol. 286(1):411–418, 1998.

Johnson, et al., "Binding to the serotonin 5–HT$_2$ receptor by the enantiomers of 125$_{I-DOI}$," *Neuropharmacology*, vol. 26,(12):1803–1806, 1987.

Wang, et al., "Effect of $_p$–MPPI hydrochloride ($_p$–MPPI) applied before 5–methylurapidil (5–MU) on intraocular pressure (IOP) in normal monkeys," *Investigative Ophthalmology & Visual Science*, vol. 39(4) S488, Mar. 15, 1998.

Chang, et al., "Mechanism of the ocular hypotensive action of ketanserin," *Journal of Ocular Pharmacology*, vol. 1(2): 137–147, 1985.

Costagliola et al., "Effect of oral ketanserin administration on intraocular pressure in glaucomatous patients," *Exp. Eye Research*, vol. 52:507–510, 1991.

Costagliola, et al., "Fluoxetine oral administration increases intraocular pressure," *British Journal Ophthalmology*, vol. 80: 678, 1996.

Ahmad, "Fluoxetine and glaucoma," *The Annals of Pharmacotherapy*, vol. 25:436, Apr. 1991. Iris–ciliary body, *Journal Neurochemistry*, vol. 53(3):686–690, 1989.

Wang, et al., "Effect of 5–methylurapidil, an α$_{1a}$–adrenergic antagonist and 5–hydroxytryptamine$_{1a}$ agonist, on aqueous Humor dynamics in monkeys and rabbits," *Current Eye Research*, vol. 16:769–775, 1997.

Osborne, et al., "Do beta–adrenoceptors and serotonin 5–HT$_{1A}$ receptors have similar functions in the control of Intraocular pressure in the rabbit?" *Ophthalmologica*, vol. 210:308–314, 1996.

Meyer–Bothling, et al., "Topical application of serotonin or the 5–HT$_1$–Agonist 5–CT intraocular pressure in rabbits," *Investigative Ophthalmology & Visual Science*, vol. 34(10):3035–3042, Sep. 1993.

Krootila, et al., "Effect of serotonin and its antagonist (Ketanserin) on intraocular pressure in the rabbit," *Journal of Ocular Pharmacology*, vol. 3(4):279–290, 1987.

SEROTONERGIC 5HT$_2$ AGONISTS FOR TREATING GLAUCOMA

This application claims priority from PCT/US99/19888 filed on Sep. 3, 1999, and U.S. Ser. No. 60/101,067, filed on Sep. 18, 1998.

The present invention is directed to the use of compounds with serotonergic 5HT$_2$ agonist activity (Compound) to treat glaucoma, which includes lowering intraocular pressure.

BACKGROUND OF THE INVENTION

Serotonin (5-hydroxytryptamine; 5HT) is an endogenous biogenic amine with a well defined neurotransmitter function in many tissues of the body including the eye [Zifa and Fillion, *Pharmacol. Rev.*, 44, 401 (1992); Hoyer et al., *Pharmacol. Rev.*, 46, 157 (1994); Tobin et al., *J. Neurosci.*, 8, 3713 (1988)].

5HT can interact with at least seven major 5HT receptors (5HT$_1$–5HT$_7$) and additional subtypes within these families to initiate intracellular biochemical events such as stimulation of second messengers (e.g. cAMP, inositol trisphosphate) eventually leading to the final biological response, for example, tissue contraction or hormone release, etc. [Hoyer et al., supra; Martin et al., *Trends Pharmacol. Sci.*, 19, 2 (1998)]. Receptor subtypes within the 5HT$_1$ family are negatively coupled to adenylyl cyclase (AC) and cause inhibition of cAMP production, while 5HT$_4$, 5HT$_6$, and 5HT$_7$ receptors are positively coupled to AC and thus stimulate cAMP production when activated by 5HT [Martin et al., supra]. The 5HT$_3$ receptor is unique in that it couples to an ion channel which gates sodium, potassium, and calcium [Hoyer et al., supra].

The receptors in the 5HT$_2$ family are positively coupled to phospholipase C (PLC) and thus generate inositol phosphates and mobilize intracellular calcium when activated by 5HT. The 5HT$_2$ receptor classification consists of the 5HT$_{2A}$, 5HT$_{2B}$, and 5HT$_{2C}$ receptor subtypes, all of which have highly homologous amino acid sequences. The receptor previously referred to as 5HT$_{1C}$ in an earlier nomenclature (prior to about 1990), has been reclassified as the 5HT$_{2C}$ receptor because of its greater similarity with other PLC coupled receptors of the 5HT$_2$ family, based on molecular cloning and its pharmacological characteristics (Hoyer, et al, 1994).

Serotonergic nerves innervate the eye [Tobin et al., *J. Neurosci.*, 8, 3713 (1988)] and 5HT has been found in the aqueous humor of human eyes [Martin et al., *Ophthalmol.*, 95, 1221 (1988)]. In addition, receptor binding sites for. [$^3$H]5HT have been demonstrated and pharmacologically characterized in the iris-ciliary body (ICB) of rabbits [Mallorga and Sugrue, *Curr. Eye Res.*, 6, 527 (1987) and Chidlow et al., *Invest. Ophthalmol. Vis. Sci.*, 36, 2238 (1995)]. These 5HT binding sites have been shown to be functionally coupled to second messenger generation in rabbits [Tobin and Osborne, *J. Neurochem.*, 53, 686 (1989) and Tobin et al., *J. Neurosci, supra*]. In the human ICB these binding sites are characterized as 5HT$_{1A}$ and 5HT$_2$ receptors [Barnet and Osborne, *Exp. Eye Res.*, 57, 209 (1993)]. In addition, the presence of mRNAs for 5HT$_{1A}$ and 5HT$_7$ receptors in the rabbit ICB have been reported [Chidlow et al., *Invest. Ophthalmol. Vis. Sci.*, supra and Osborne and Chidlow, *Ophthalmologica*, 210, 308 (1996)]. The precise functions of these receptors in the eye are unknown.

5HT or 5-carboxamidotryptamine (5-CT) topically applied to the rabbit eye raise intraocular pressure (IOP) [Meyer-Bothling et al., *Invest. Ophthalmol. Vis. Sci.*, 34, 3035 (1993)]. By contrast, another group has shown that topically applied 5HT decreased IOP in the rabbit; however, when 5HT was administered to the rabbit intracarnerally it resulted in an increase in IOP and caused breakdown of the blood-aqueous barrier [Krootila et. al., *J. Ocular Pharmacol.*, 3, 279 (1987)]. In addition, the 5HT uptake inhibitor, fluoxetine (Prozac®), also raises IOP in human subjects upon oral administration [Costagliola et al., *Br. J Ophthalmol.*, 80, 678 (1996)] and may cause glaucoma [Ahmad *Ann. Pharmacother.*, 25, 436 (1992)]. However, the 5HT receptor subtype(s) involved in the IOP-elevating effects of 5HT, 5-CT and fluoxetine are unknown.

Studies conducted in rabbits with 8-hydroxy DPAT and MKC-242 (5HT$_{1A}$ agonists) have shown these compounds lower IOP [Osborne and Chidlow *Ophthalmologica*, 210, 308 (1996), and EP 0771563-A2]. In addition, 5-methylurapidil (5HT$_{1A}$ agonist) lowered IOP in glaucomatous monkeys [Wang et al., *Curr. Eye Res.*, 16, 679 (1997)]. Both MKC-242 and 5-methylurapidil are relatively potent α$_1$ receptor antagonists (α$_1$ antagonists are known to lower IOP in rabbits, monkeys, and man). The mechanism of action for lowering IOP by 5-methylurapidil has been attributed to its α$_1$ antagonist activity and not its 5HT$_{1A}$ agonist activity [Wang et al., *Invest. Ophthal Vis. Sci.*, 39(Suppl), 2236 (1998)]. U.S. Pat. No. 5,693,654, discloses 5HT$_1$-like (now designated 5HT$_{1D}$) receptor agonists, such as sumatriptan, for lowering IOP. WO92/20338 discloses certain 5HT$_{1A}$ antagonists for the treatment of glaucoma.

Methysergide (5HT$_2$ antagonist, but with other activities) lowered IOP in rabbits [Krootila et al., *Exp. Eye Res.*, supra]. Ketanserin (5HT$_{2A/C}$ antagonist), also with significant α$_1$ antagonist activity, lowers IOP in rabbits and man [Chan et al., *J. Ocular Pharmacol.*, 1, 137 (1985) and Costagliola et al., *Exp. Eye Res.*, 52, 507 (1991)]. Saprogrelate (5HT$_{2A}$ antagonist) lowers IOP in rabbits and in man when dosed topically or orally [Mano et al., *Invest. Ophthal. Vis. Sci.*, 36(Suppl), 3322 (1995) and Takenaka et al., *Invest Ophthal. Vis. Is Sci.*, 36(Suppl), 3390 (1995)]. EP 522226 and U.S. Pat. No. 5,290,781 disclose the use of ketanserin and its derivatives for treating ocular hypertension. U.S. Pat. Nos. 5,290,781 and 5,106,555 disclose the use of certain 5HT$_2$ antagonists for lowering IOP. U.S. Pat. No. 5,652,272 discloses saprogrelate for reducing IOP. U.S. Pat. No. 5,538,974 discloses ophthalmic compositions of certain 5HT$_2$ antagonists for lowering IOP. WO/9911619 discloses 5HT$_{2A}$ antagonists which may be efficacious in treating glaucoma.

U.S. Pat. No. 5,011,846 discloses certain 5HT$_3$ receptor antagonists for treating glaucoma.

WO 97/17345 discloses that particular compounds with 5HT$_4$ serotonergic receptor agonist or antagonist activity are useful for treating psychiatric, gastrointestinal, lower urinary, and cardiovascular disorders. The publication mentions the compounds may also be useful for glaucoma.

As evidenced by the previous discussion, it is not clear which serotonergic receptor activity is responsible for lowering IOP. Moreover, a number of these compounds are known to have activity at non-serotonergic receptors which are known to be involved in lowering IOP.

SUMMARY OF THE INVENTION

The present invention is directed to the use of compounds with 5HT$_2$ receptor agonist activity to treat glaucoma, which includes lowering intraocular pressure. Compositions of the compounds are contemplated for such uses.

DETAILED DESCRIPTION PREFERRED EMBODIMENTS

Unexpectedly, it has been found that serotonergic compounds which possess agonist activity at 5HT$_2$ receptors effectively lower and control elevated IOP and are useful for treating glaucoma.

Specific compounds which exemplify the present invention include: 1) (R)4-iodo-2,5 dimethoxy-α-methyl-benzeneethanamine [(R)-DOI], the prototypical selective 5HT$_2$ agonist which is not selective amongst the 5HT$_2$ receptor subtypes [Baxter et al., *Trends. Pharmacol. Sci.*, 16, 105 (1995)]; 2) α-methyl-serotonin, a potent 5HT$_2$ agonist with modest receptor subtype selectivity: 5HT$_{2B}$>5HT$_{2C}$>5HT$_{2A}$ [Baxter, et al., supra]; 3) 5-methoxy-α-methyltryptamine, with a profile similar to that of α-methyl-serotonin [Nichols et al., *J. Med. Chem.*, 31, 1406 (1998)]. The following references are not limiting, but rather exemplify Compounds useful according to the present invention and are incorporated herein by reference: U.S. Pat. Nos. 5,861,425; 5,646,173; 5,578,612; 5,571,833; 5,545,644; 5,494,928; 4,659,706 and 4,487,773; published European Patent Specification No. 863,136; published International Patent Application Nos. WO98/56768; WO98/31354; WO98/30548; WO98/30546. Additionally, compounds disclosed in the following publications further exemplify Compounds useful according to the present invention and are also incorporated herein by reference: Parker et al, *J. Med. Chem.* 41, 5148 (1998); Vangveravong et al, *J. Med. Chem.* 41, 4995 (1998); Albertini et al, *Mutagenesis*, 13, 397 (1998); Monte et al, *J. Med. Chem.* 40, 2997 (1997); Bös et al., *Eur. J. Med Chem.*, 32, 253 (1997); Bös et al., *J. Med. Chem.*, 40, 2762 (1997); Monte et al, *J. Med Chem.* 39, 2952 (1996); Glennon et al., *J Med. Chem.*, 37, 1929 (1994); Macor et al, *Tetrahedron Lett.* 35, 45 (1994); Macor et al, *J. Med Chem.* 35, 4503 (1992); Macor et al. *J. Med. Chem.*, 35, 3625 (1992); Glernon et al, *J. Med. Chem.* 35, 734 (1992); Seggel et al. *J. Med Chem.* 33, 1032 (1990).

It is recognized that many of the aforementioned Compounds have asymmetric atoms, therefore all enantiomers and diastereomers are contemplated. Also contemplated are pharmaceutically acceptable salts as well as the free bases of the Compounds. The Compounds are administered to the eye (e.g., topically, intracamerally, or via an implant). The Compounds are preferably incorporated into topical ophthalmic formulations for delivery to the eye. The Compounds may be combined with ophthalmologically acceptable preservatives, surfactants, viscosity enhancers, penetration enhancers, buffers, sodium chloride, and water to form an aqueous, sterile ophthalmic suspension or solution. Ophthalmic solution formulations may be prepared by dissolving a Compound in a physiologically acceptable isotonic aqueous buffer. Further, the ophthalmic solution may include an ophthalmologically acceptable surfactant to assist in dissolving the Compound. Furthermore, the ophthalmic solution may contain an agent to increase viscosity, such as, hydroxymethylcellulose, hydroxyethylcellulose, hydroxypropylmethylcellulose, methylcellulose, polyvinylpyrrolidone, or the like, to improve the retention of the formulation in the conjunctival sac. Gelling agents can also be used, including, but not limited to, gellan and xanthan gum. In order to prepare sterile ophthalmic ointment formulations, the active ingredient is combined with a preservative in an appropriate vehicle, such as, mineral oil, liquid lanolin, or white petrolatum. Sterile ophthalmic gel formulations may be prepared by suspending the active ingredient in a hydrophilic base prepared from the combination of, for example, carbopol-940, or the like, according to the published formulations for analogous ophthalmic preparations; preservatives and tonicity agents can be incorporated.

The Compounds are preferably formulated as topical ophthalmic suspensions or solutions, with a pH of about 5 to 8. The Compounds will normally be contained in these formulations in an amount 0.01% to 5% by weight, but preferably in an amount of 0.25% to 2% by weight. Thus, for topical presentation 1 to 2 drops of these formulations would be delivered to the surface of the eye 1 to 4 times per day according to the routine discretion of a skilled clinician.

The Compounds can also be used in combination with other agents for treating glaucoma, such as, but not limited to, β-blockers, prostaglandins, carbonic anhydrase inhibitors, α$_2$ agonists and miotics. The Compounds can also be used with calcium channel blockers and antagonists for metabotropic and ionotropic glutamate receptors and/or antagonists for their associated binding sites, such as, the polyamine and strychnine-insensitive glycine sites. These agents may be administered topically, but usually systemically.

A particularly preferred combination includes the use of a Compound with an α$_2$ adrenergic agent, such as, apraclonidine or brimonidine or their pharmaceutically acceptable salts.

Compounds useful in this invention can be identified using methodology well known to one skilled in the art. The selection is made first by using a 5HT$_2$ receptor binding assay, an example of which is described below. Compounds of this invention posses high affinity for 5HT$_2$ receptors (IC$_{50}$ or K$_i$ values of about 20 nM or less and this affinity is higher than at other 5HT receptors). The second part of this selection is made based on the functional activity of the compound as described below. Compounds of this invention possess agonist EC$_{50}$ values of about 1 μM or less. Antagonists are not contemplated in this invention.

Both of these methods are believed to be the best way to identify a compound that would be useful according to this invention; however, it is important to note that some compounds that are identified by these methods may not be as desirable as others as commercial products. One must take into account the nature of the compound in question in terms of its structure, physical properties—e.g., solubility, lipophilicity, and chemical stability and its susceptibility to be metabolized to an inactive compound (or compounds) within the eye. The impact of these parameters is well known to one skilled in the art and can be determined using methods well known in the art.

In addition to the above discussion, certain 5HT$_2$ agonists such as DOI, its isomers, and related compounds are known to cause central nervous system (CNS) side effects in man when dosed systemically. In the present invention it is believed that the Compounds can be dosed topically, at a low enough dose to lower and control IOP, but not cause unwanted CNS side effects which may be associated with some Compounds. Some Compounds are particularly desirable because their physical properties keep them from penetrating the CNS and causing side effects. Also, certain Compounds of this invention may cause local irritation and discomfort upon topical ocular administration that render them less desirable than other more comfortable compounds. This can be readily determined using methods well known in the art.

EXAMPLE 1

5HT$_2$ Receptor Binding Assay

In order to determine the relative affinities of serotonergic compounds at the 5HT$_2$ receptors, their ability to compete for the binding of the agonist radioligand [$^{125}$I]DOI to brain is 5HT$_2$ receptors is determined as described below with minor modification of the methods of Johnson et al. (*Neuropharmacology*, 26, 1803 (1987)). Aliquots of post mortem rat or human cerebral cortex homogenates (400 µl) dispersed in 50 mM TrisHCl buffer (pH 7.4) are incubated with [$^{125}$I]DOI (80 pM final) in the absence or presence of methiothepin (10 µM final) to define total and non-specific binding, respectively, in a total volume of 0.5 ml. The assay mixture is incubated for 1 hr at 23° C. in polypropylene tubes and the assays terminated by rapid vacuum filtration over Whatman GF/B glass fiber filters previously soaked in 0.3% polyethyleneimine using ice-cold buffer. Test compounds (at different concentrations) are substituted for methiothepin. Filter-bound radioactivity is determined by scintillation spectrometry on a beta counter. The data are analysed using a non-linear, iterative curve-fitting computer program (Bowen & Jerman, *Trends Pharmacol. Sci.*, 16, 413 (1995)) to determine the compound affinity parameter. The concentration of the compound needed to inhibit the [$^{125}$I] DOI binding by 50% of the maximum is termed the $IC_{50}$ or $K_i$ value. Compounds are considered to possess high affinity for the $5HT_2$ receptor if their $IC_{50}$ or $K_i$ values are $\leq 50$ nM.

$5HT_2$ Functional Assay: Phosphoinositide (PI) Turnover Assay

The relative agonist activity of serotonergic compounds at the $5HT_2$ receptor can be determined in vitro using the ability of the compounds to stimulate the production of [$^3$H]inositol phosphates in [$^3$H]myo-inositol-labeled A7r5 rat vascular smooth muscle cells by their ability to activate the enzyme phospholipase C. These cells are grown in culture plates, maintained in a humidified atmosphere of 5% $CO_2$ and 95% air and fed semi-weekly with Dulbecco's modified Eagle medium (DMEM) containing 4.5 g/l glucose and supplemented with 2mM glutamine, 10 µg/ml gentamicin, and 10% fetal bovine serum. For the purpose of conducting the phosphoinositide (PI) turnover experiments, the A7r5 cells are cultured in 24-well plates as previously described (Griffin et al., *J. Pharmacol. Expt. Ther.*, 286, 411 (1998)). Confluent cells are exposed for 24–30 hrs to 1.5 µCi [$^3$H]-myo-inositol (18.3 Ci/mmol) in 0.5 ml of serum-free medium. Cells are then rinsed once with DMEM/F-12 containing 10 mM LiCl prior to incubation with the test agent (or solvent as the control) in 1.0 ml of the same medium for 1 hr at 37° C., after which the medium is aspirated and 1 ml of cold 0.1 M formic acid added to stop the reaction. The chromatographic separation of [$^3$H]-inositol phosphates ([$^3$H]-IPs) on an AG-1-X8 column is performed as previously described (Griffin et al., *J. Pharmacol. Expt. Ther.*, 286, 411 (1998)) with sequential washes with $H_2O$ and 50 mM ammonium formate, followed by elution of the total [$^3$H]IPs fraction with 1.2 M ammonium formate containing 0.1 M formic acid. The eluate (4 ml) is collected, mixed with 15 ml scintillation fluid, and the total [$^3$H]-IPs determined by scintillation counting on a beta-counter. Concentration-response data are analyzed by the sigmoidal fit function of the Origin Scientific Graphics software (Microcal Software, Northampton, Mass.) to determine agonist potency ($EC_{50}$ value) and efficacy ($E_{max}$). Serotonin (5HT) is used as a positive control (standard) agonist compound and the efficacy of test compounds is compared to that of 5HT (set at 100%). The concentration of the compound needed to stimulate the production of [$^3$H]-IPs by 50% of the maximum response is termed the $EC_{50}$ value. Compounds are considered potent agonists if their $EC_{50}$ values in this functional assay are $\leq 1$ µM and are considered full agonists if their efficacy is >80% of that of 5HT.

The above procedures were used to generate the data shown in Table 1.

TABLE 1

$5HT_2$ Receptor Binding and Functional Data for Representative Compounds.

| Compound | $IC_{50}$, nM (SEM) | $EC_{50}$, nM (SEM) | Efficacy ($E_{max}$, %) |
|---|---|---|---|
| (R)-DOI | 0.5 ± 0.2 | 277 ± 35 | 82 |
| α-Methylserotonin | 3.5 ± 0.9 | 189 ± 26 | 104 |
| 5-Methoxy-α-methyltryptamine | 2.5 ± 0.9 | 286 ± 39 | 107 |
| Serotonin | 0.8 ± 0.2 | 338 ± 27 | 100 |

Acute IOP Response in Lasered (Hypertensive) Eyes of Conscious Cynomolgus Monkeys Intraocular pressure (IOP) was determined with an Alcon Pneumatonometer after light corneal anesthesia with 0.1% proparacaine. Eyes were washed with saline after each measurement. After a baseline IOP measurement, test compound was instilled in one 30 µL aliquot to the right eyes only of nine cynomolgus monkeys. Vehicle was instilled in the right eyes of six additional animals. Subsequent IOP measurements were taken at 1, 3, and 6 hours.

The profile of the IOP response following topical administration for each of these Compounds is provided in Table 2.

TABLE 2

IOP Response for Representative Compounds

| Example | Dose, µg | Baseline IOP (mmHg) | Percent IOP Reduction ± SEM Hours after dose | | |
|---|---|---|---|---|---|
| | | | 1 | 3 | 6 |
| (R)-DOI | 100 | 31.9 | 11.0 ± 4.98 | 25.3 ± 2.97 | 34.4 ± 4.98 |
| α-Methyl-serotonin | 250 | 41.8 | 14.2 ± 4.39 | 25.8 ± 5.16 | 30.8 ± 7.72 |
| 5-Methoxy-α-methyl-tryptamine | 300 | 38.1 | 21.6 ± 5.05 | 35.2 ± 6.12 | 33.4 ± 5.39 |
| Serotonin | 250 | 33.5 | 13.3 ± 5.31 | 18.0 ± 5.12 | 2.0 ± 7.39 |

The following topical ophthalmic formulations are useful according to the present invention administered 1–4 times per day according to the discretion of a skilled clinician.

EXAMPLE 2

| Ingredients | Amount (wt %) |
|---|---|
| $5HT_2$ Compound | 0.01–2% |
| Hydroxypropyl methylcellulose | 0.5% |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.3–7.4 |
| Purified water | q.s. to 100% |

EXAMPLE 3

| Ingredients | Amount (wt %) |
| --- | --- |
| 5HT$_2$ Compound | 0.01–2% |
| Hydroxypropyl methylcellulose | 0.5% |
| Cremophor EL | 0.1% |
| Tromethamine, USP, AR | 0.64% |
| Mannitol, USP | 3.0% |
| Boric acid, USP | 0.3% |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.3–7.4 |
| Purified water | q.s. to 100% |

EXAMPLE 4

| Ingredients | Amount (wt %) |
| --- | --- |
| 5HT$_2$ Compound | 0.01–2% |
| Methyl cellulose | 4.0% |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.3–7.4 |
| Purified water | q.s. to 100% |

EXAMPLE 5

| Ingredients | Amount (wt %) |
| --- | --- |
| 5HT$_2$ Compound | 0.01–2% |
| Hydroxypropyl-β-cyclodextrin | 4.0% |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.3–7.4 |
| Purified water | q.s. to 100% |

EXAMPLE 6

| Ingredients | Amount (wt %) |
| --- | --- |
| 5HT$_2$ Compound | 0.01–2% |
| Xanthan gum | 0.5–6.0% |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.3–7.4 |
| Purified water | q.s. to 100% |

EXAMPLE 7

| Ingredients | Amount (wt %) |
| --- | --- |
| 5HT$_2$ Compound | 0.01–2% |
| Guar gum | 0.4–6.0% |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.3–7.4 |
| Purified water | q.s. to 100% |

EXAMPLE 8

| Ingredients | Amount (wt %) |
| --- | --- |
| 5HT$_2$ Compound | 0.01–2% |
| Tyloxapol | 0.2–4.0% |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.3–7.4 |
| Purified water | q.s. to 100% |

EXAMPLE 9

| Ingredients | Amount (wt %) |
| --- | --- |
| 5HT$_2$ Compound | 0.01–2% |
| White petrolatum and mineral oil and lanolin | Ointment consistency |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.3–7.4 |

EXAMPLE 10

| Ingredients | Amount (wt %) |
| --- | --- |
| 5HT$_2$ Compound | 0.01–2% |
| Brimonidine | 0.2% |
| Hydroxypropyl methylcellulose | 0.5% |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.3–7.4 |
| Purified water | q.s. to 100% |

We claim:

1. A method for treating glaucoma which comprises administering to a person in need thereof, a composition comprising a pharmaceutically effective amount of a compound with 5HT$_2$ receptor agonist activity.

2. The method of claim 1 wherein the 5HT$_2$ receptor agonist is present at a concentration of 0.01 weight percent to 5 weight percent.

3. The method of claim 2 wherein the concentration is 0.25 weight percent to 2 weight percent.

4. The method of claim 1 wherein the $5HT_2$ receptor agonist is (R)-DOI, α-Methylserotonin, 5-Methoxy-α-methyltryptamine.

5. The method of claim 1 wherein the composition additionally comprises another compound selected from the group consisting of β-blockers, prostaglandins, carbonic anhydrase inhibitors, $α_2$ agonists, and miotics.

6. The method of claim 5 wherein the compound is an $α_2$ agonist.

7. The method of claim 6 wherein the $α_2$ agonist is selected from the group consisting of apraclonidine and brimonidine.

8. The method of claim 5 wherein the compound is a prostaglandin.

9. The method of claim 5 wherein the compound is a carbonic anhydrase inhibitor.

10. The method of claim 5 wherein the compound is a β-blocker.

11. The method of claim 5 wherein the compound is a miotic.

* * * * *